(12) United States Patent
Biedermann

(10) Patent No.: US 10,828,076 B2
(45) Date of Patent: Nov. 10, 2020

(54) BONE FIXATION ASSEMBLY WITH ENLARGED ANGLE OF INCLINATION FOR A BONE ANCHOR TO A FAVORED SIDE

(71) Applicant: Biedermann Technologies GmbH & Co. KG, Donaueschingen (DE)

(72) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 197 days.

(21) Appl. No.: 15/982,488

(22) Filed: May 17, 2018

(65) Prior Publication Data
US 2019/0350628 A1 Nov. 21, 2019

(51) Int. Cl.
*A61B 17/80* (2006.01)

(52) U.S. Cl.
CPC ................ *A61B 17/8057* (2013.01)

(58) Field of Classification Search
CPC combination set(s) only.
See application file for complete search history.

(56) References Cited

U.S. PATENT DOCUMENTS

| | | | |
|---|---|---|---|
| 6,139,550 A | 10/2000 | Michelson | |
| 6,322,562 B1 | 11/2001 | Wolter | |
| 6,623,486 B1 | 9/2003 | Weaver et al. | |
| 7,033,394 B2 | 4/2006 | Michelson | |
| 7,229,445 B2 | 6/2007 | Hayeck et al. | |
| 7,951,178 B2 | 5/2011 | Jensen | |
| 8,142,485 B2 | 3/2012 | Buhren et al. | |
| 8,277,493 B2 | 10/2012 | Farris et al. | |
| 8,323,543 B2 | 12/2012 | Michelson | |

(Continued)

FOREIGN PATENT DOCUMENTS

| | | |
|---|---|---|
| CN | 201692038 U | 1/2011 |
| JP | H10501444 A | 2/1998 |

(Continued)

OTHER PUBLICATIONS

"Dynamic Compression Principle", Lorich et al., AO Surgery Reference, Aug. 1, 2014, (taken from Reudi TP Buckley R. Moran GC (2007) AO Principles of Fracture Management. 2nd ed vol. 1. Shutgart New York; (ThiemeVerlag) (2 pages) https://www2.aofoundation.org/wps/portal/lut/ pa0/04_Sj9CPykssy0xPLMnMz0vMAfGjzOKN_A0M3D2DDbz9 . . . .

(Continued)

*Primary Examiner* — Matthew J Lawson
(74) *Attorney, Agent, or Firm* — Gordon & Jacobson, P.C.

(57) ABSTRACT

A plate member assembly is provided for use in orthopaedic or trauma surgery. The plate member assembly includes a plate member having a top side and a bottom side with at least one passage extending therethrough. The at least one passage includes a first bore with a first end open towards the top side, a seat portion configured to receive the head of the bone anchor, and a second bore open towards the bottom side. The first bore comprises a first central axis and the seat portion comprises a second central axis. The anchor can be angled within the seat portion relative to the second central axis. Recesses are provided at the first bore and second bore to permit the bone anchor to be further angled in a favored direction relative to the second central axis.

43 Claims, 8 Drawing Sheets

(56) References Cited

U.S. PATENT DOCUMENTS

| | | |
|---|---|---|
| 8,343,196 B2 | 1/2013 | Schneider |
| 8,409,260 B2 | 4/2013 | Biedermann et al. |
| 8,632,545 B2 | 1/2014 | Sarangapani et al. |
| 8,740,955 B2 | 6/2014 | Bottlang et al. |
| 8,808,335 B2 | 8/2014 | Biedermann |
| 10,052,142 B2 | 8/2018 | Biedermann |
| 2002/0016595 A1 | 2/2002 | Michelson |
| 2002/0022843 A1 | 2/2002 | Michelson |
| 2002/0183752 A1 | 12/2002 | Steiner et al. |
| 2006/0264946 A1 | 11/2006 | Young |
| 2007/0043366 A1 | 2/2007 | Pfefferle et al. |
| 2007/0055249 A1 | 3/2007 | Jensen et al. |
| 2008/0051786 A1 | 2/2008 | Jensen |
| 2008/0249573 A1 | 10/2008 | Buhren |
| 2012/0059425 A1 | 3/2012 | Biedermann |
| 2012/0203348 A1 | 8/2012 | Michelson |
| 2014/0066998 A1* | 3/2014 | Martin ............... A61B 17/8057 606/308 |
| 2014/0271029 A1* | 9/2014 | Arnett .................... F16B 39/28 411/259 |
| 2015/0094775 A1 | 4/2015 | Thomas et al. |
| 2015/0320462 A1* | 11/2015 | Biedermann ...... A61B 17/8057 606/291 |
| 2018/0000496 A1 | 1/2018 | Langdale et al. |
| 2018/0064477 A1* | 3/2018 | Lopez ................ A61B 17/8033 |
| 2019/0328430 A1* | 10/2019 | Bosshard ........... A61B 17/8057 |

FOREIGN PATENT DOCUMENTS

| | | |
|---|---|---|
| JP | 2001525702 A | 12/2001 |
| WO | WO01/26566 A1 | 4/2001 |
| WO | WO2009/063489 A2 | 5/2009 |
| WO | WO2011/109127 A1 | 9/2011 |

OTHER PUBLICATIONS

Extended European Search Report for corresponding European Application No. 14200086.8-1506, European Search Report dated Mar. 24, 2015 and dated Apr. 2, 2015 (6 pages).

Extended European Search Report dated Oct. 28, 2019 of application No. EP19174971.

* cited by examiner

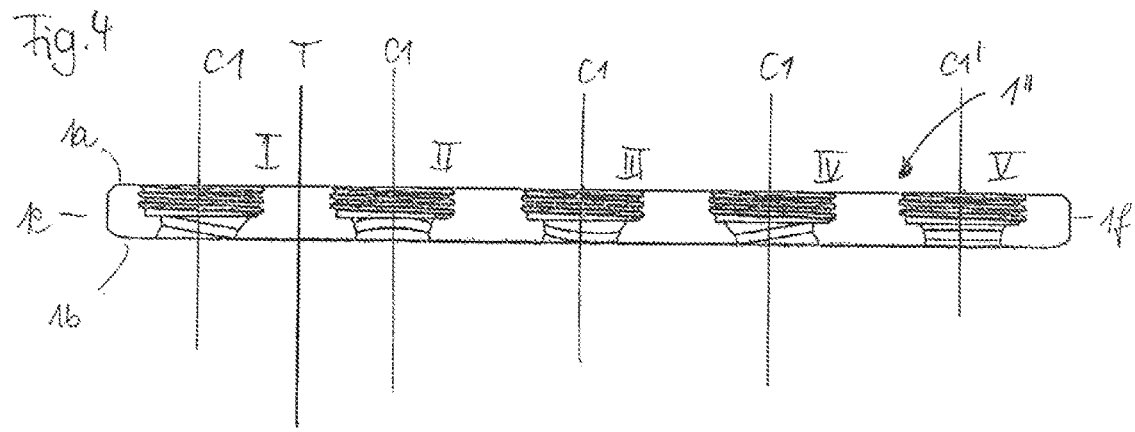
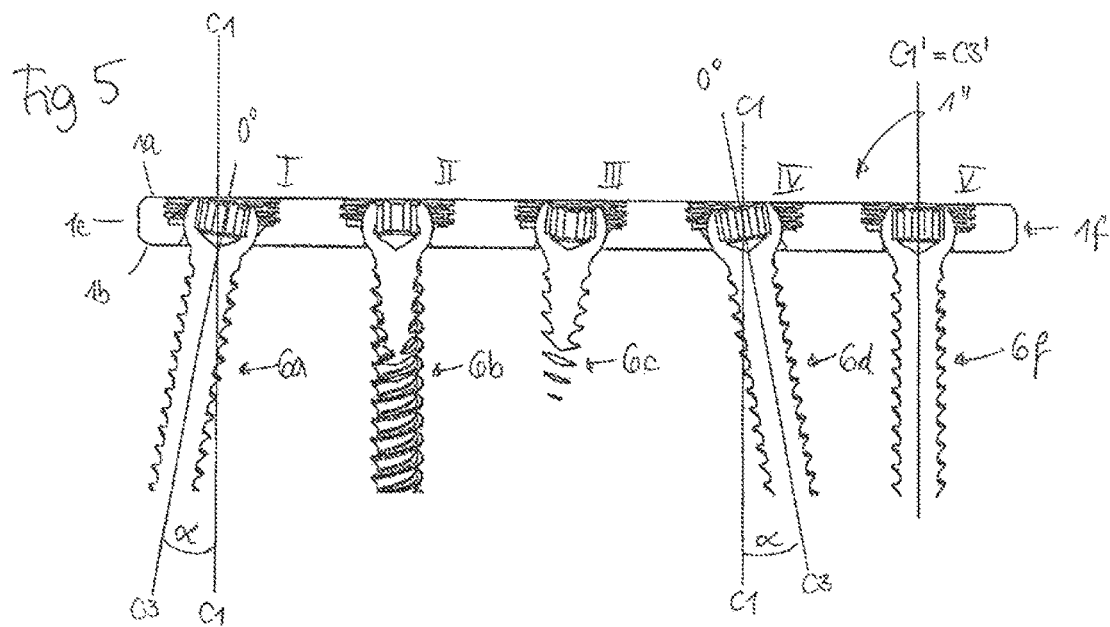
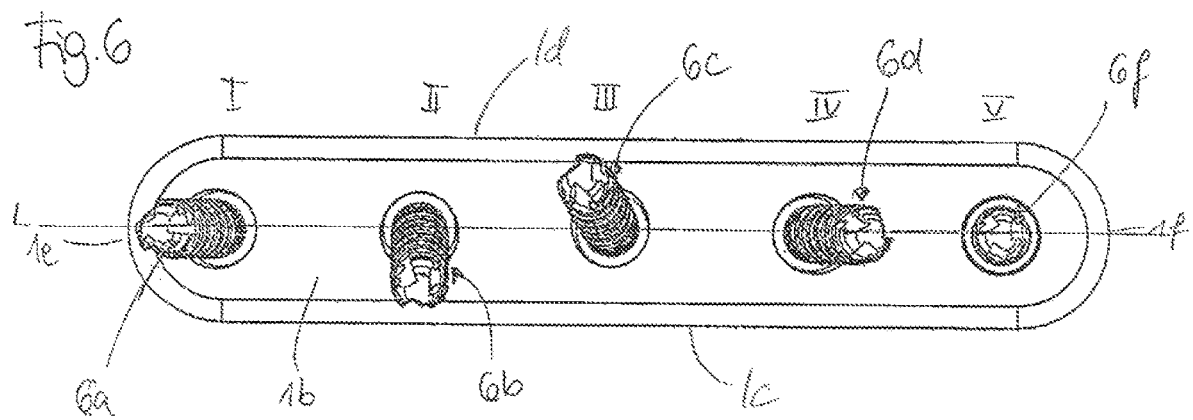

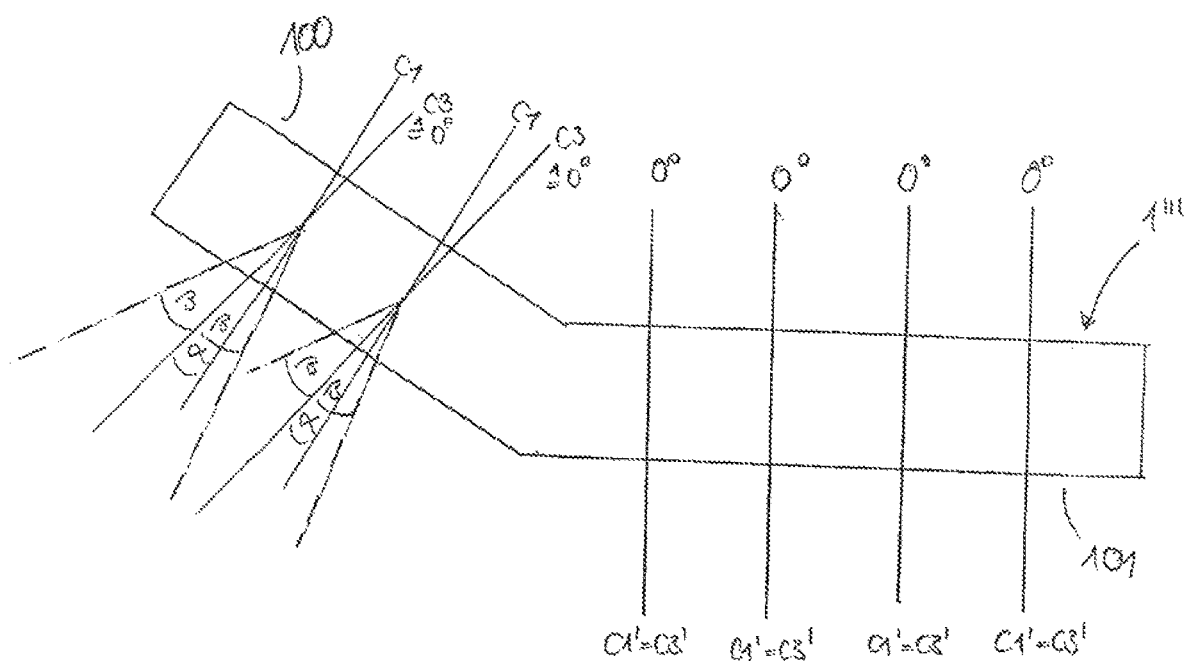

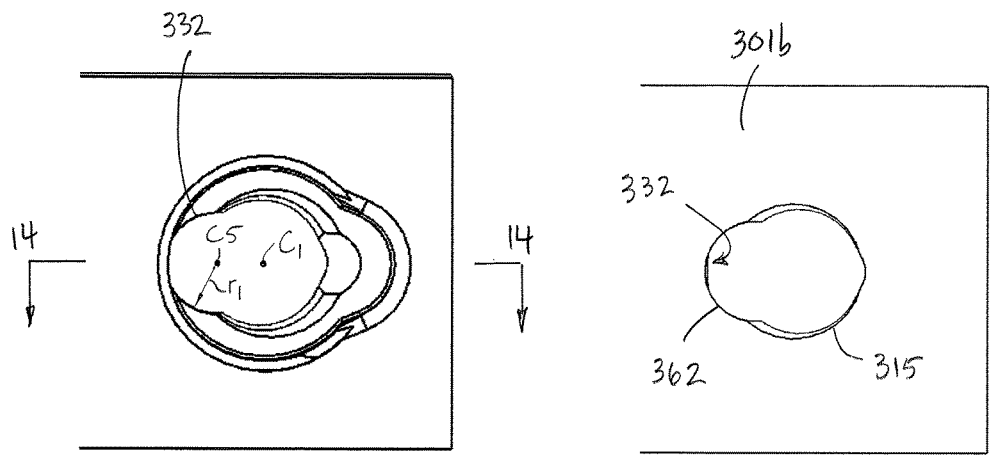
FIG. 13
FIG. 15
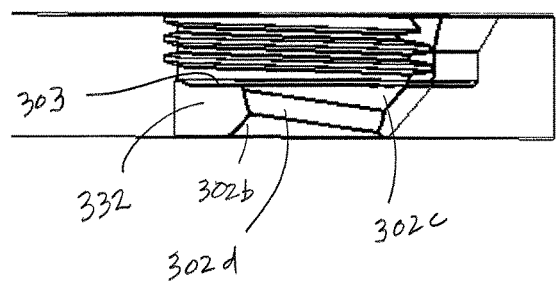
FIG. 14

BONE FIXATION ASSEMBLY WITH ENLARGED ANGLE OF INCLINATION FOR A BONE ANCHOR TO A FAVORED SIDE

CROSS-REFERENCE TO RELATED APPLICATIONS

This application is related to U.S. Ser. No. 14/688,970, filed Apr. 16, 2015, which claims the benefit of U.S. Provisional Patent Application Ser. No. 61/981,058, filed Apr. 17, 2014, the entire contents of which are hereby incorporated by reference.

BACKGROUND

Field

The invention relates to a bone fixation assembly for the immobilization of bones or bone fragments. Particularly, the invention relates to a bone fixation assembly comprising a bone plate and a bone anchor, the bone fixation assembly allowing an enlarged angle of inclination to one side for the bone anchor with respect to a vertical axis through the plate at a position of a bone anchor hole.

State of the Art

US 2012/0059425 A describes a bone fixation assembly with a polyaxial coupling between the bone anchors of the bone plate assembly and the plate member with an increased range of angular motion and a low profile.

Lorich DdG and Gardner M J describe a limited-contact dynamic compression plate assembly with elongated holes allowing 25° inclination of a bone anchor in the longitudinal plane, and up to 7° inclination in the transversal plane (Ruedi T P, Buckley R, Moran C G (2007) *AO Principles of Fracture Management.* 2nd ed. Vol. 1. Stuttgart N.Y.: Thieme-Verlag).

In the field of spinal surgery, U.S. Pat. No. 8,409,260 B2 describes a bone fixation assembly with a bone anchor and a receiving part allowing an enlarged pivot angle of the bone anchor to one side.

While the known bone fixation assemblies can provide polyaxial adjustment of the bone screws relative to the bone plate with an equal angle of inclination to each opposing side, there is still a need for an improved bone plate assembly which allows for an increased angle of inclination with respect to a vertical axis through the plate at a position of a bone anchor hole to a favored side, while still providing a low profile of the plate-screw construct as well as high stability. For example, there might be anatomical situations where the angle of inclination relative to a vertical axis through the plate at a position of a bone anchor hole should be increased to only one side. This may be the case, for example, in the context of fractures of the hand or the shoulder.

SUMMARY

According to an aspect of embodiments of the present invention, a bone fixation assembly allows a polyaxial adjustment of the bone anchor and a plate element with an enlarged angle of inclination to one side, while simultaneously providing a low profile in terms of a low thickness and a high angular stability.

Aspects and features of embodiments of the present invention are described herein with respect to some exemplary embodiments and are set forth in the claims.

A bone fixation assembly according to one or more embodiments of the present invention comprises a seat for the bone anchor, the central axis of which is inclined with respect to a vertical axis through the plate member at a position of the bone anchor hole. The seat is configured to allow insertion of the bone anchor up to around 20° with respect to the Zero-position of the bone anchor in the seat corresponding to a total range of motion of up at least 40°. Due to the design of the holes in the plate member, particularly the inclined position of the seat for the bone anchor, the motion cone is tilted so as to provide an increased angulation to a favored side. Further, circumferential portions of the upper and lower surface of the plate surrounding the plate hole are removed to permit an even increased angulation of the screw toward the favoured side without interference by the plate member. Hence, e.g. an increased insertion angle of 40° to one side can be reached.

In certain anatomical situations the plate member might be angled, for example a distal radius plate in hand surgery. In this event, the present invention provides an enlarged angle of inclination in the favored direction of the angled portion of the plate member without increasing the thickness of the plate. Moreover, in case of a locking bone plate, a thread axis of the thread for the locking screw can be provided perpendicular to the surface of the bone plate. Therefore, conical threaded holes or inclined threaded holes may be avoided.

The number of holes as well as their design defining the desired side of the enlarged angle of inclination can be adapted to the anatomical requirements easily, thus providing a high variety of applications.

The bone anchor may be fixed relative to the plate member by a locking element. With the locking element, the angular stability of the bone anchor may be increased and the bone anchor may be secured against pull-out. Different locking elements can be provided to achieve either full locking or frictional locking or to allow free angulation while only preventing pull-out of the bone anchor. Besides its application as a locking plate member of the bone fixation assembly according to the invention, the fixation assembly can also be used without a locking element, i.e. as a non-locking plate.

The bone fixation assembly according to the invention may have one hole or more than one hole, i.e. a plurality of holes dependent on the clinical application. Furthermore, the plate member may have offset holes which are offset from a central longitudinal line for more variety of usage. The plate member can be designed to have a minimal bone contact area and can be used as a dynamic plate. Also, the plate member may be contoured to provide a specific shape for specific clinical applications.

The bone plate assembly is suitable for various clinical applications. For example, the bone plate assembly is suitable for applications in areas including bones or bone parts, where an increased angle between the bone plate and the bone anchor is advantageous so as to best adapt to the anatomical situation, for example in the context of fractures of the hand or the shoulder. The design of the holes leads to a low profile of the whole bone plate assembly rendering it suitable for the application in areas with minimum soft tissue coverage such as in the case of the hand or the pelvis.

BRIEF DESCRIPTION OF THE DRAWINGS

Further features and advantages of the present invention will become apparent from the description of some embodiments with reference to the accompanying drawings. In the drawings:

FIG. 4 shows a schematic cross-sectional view of a plate member of a bone fixation assembly with several holes according to an embodiment;

FIG. 5 shows a schematic cross-sectional view of the bone fixation assembly according to FIG. 4, with several holes, screws and locking elements;

FIG. 6 shows a bottom view of the bone fixation assembly according to FIG. 5;

FIG. 7 shows a sectional view of an angled bone plate with schematic motion cones according to an embodiment;

FIG. 13 shows a schematic top view of a plate member of a bone fixation assembly according to an embodiment;

FIG. 14 shows a schematic cross-sectional view across line 14-14 in FIG. 13;

FIG. 15 shows a schematic bottom view of the plate member of FIG. 13;

DETAILED DESCRIPTION

Figure 1:
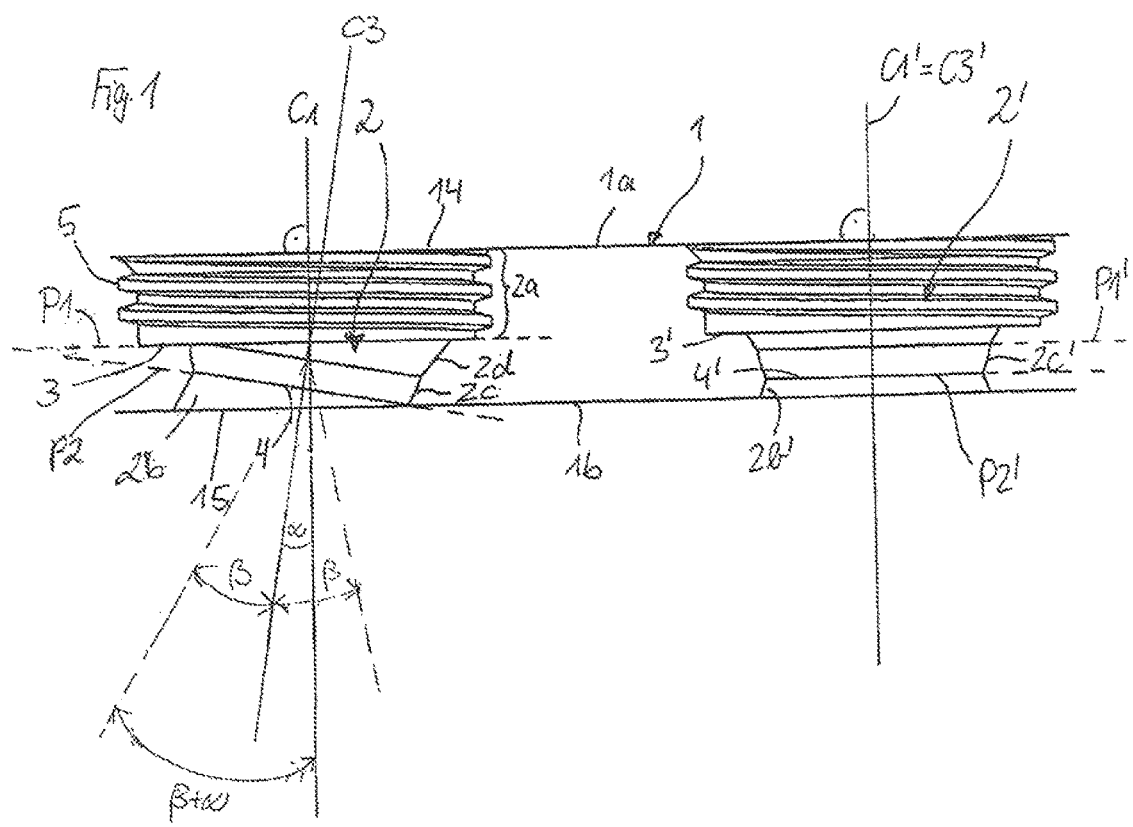
FIG. 1 shows a schematic cross-sectional view of a plate member of a bone fixation assembly with a hole, according to a first embodiment.
Figure 2:
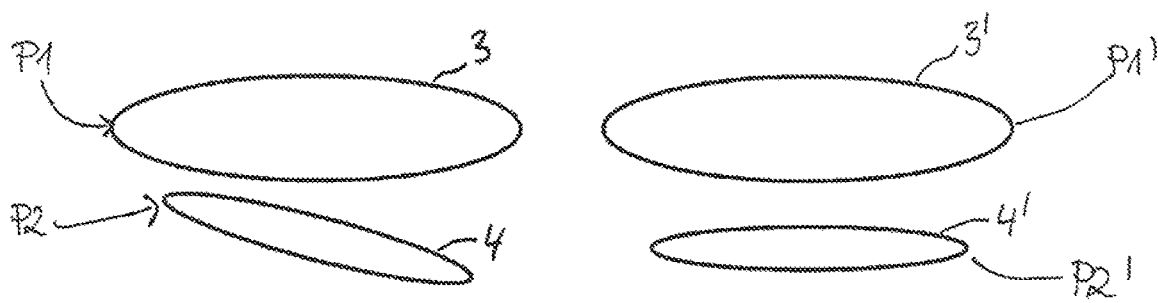
FIG. 2 shows a schematic view of the geometrical arrangement of the edges and planes defining the hole and the seat in FIG. 1.

A first embodiment of the bone fixation assembly will now be described with reference to FIGS. 1 to 3. The bone fixation assembly of the first embodiment is of the locking type, but can also be used as a non-locking plate. As can be seen in FIG. 1, the bone fixation assembly includes a plate member 1 with a top side 1a, a bottom side 1b, the top side 1a and the bottom side 1b being substantially parallel to each other. A hole forming a passage 2 extends through the plate member 1 from the top side 1a to the bottom side 1b. The passage 2 is formed by three bores 2a, 2b, 2d and a seat portion 2c therebetween that is configured to receive the head of a bone anchor.

Figure 3:
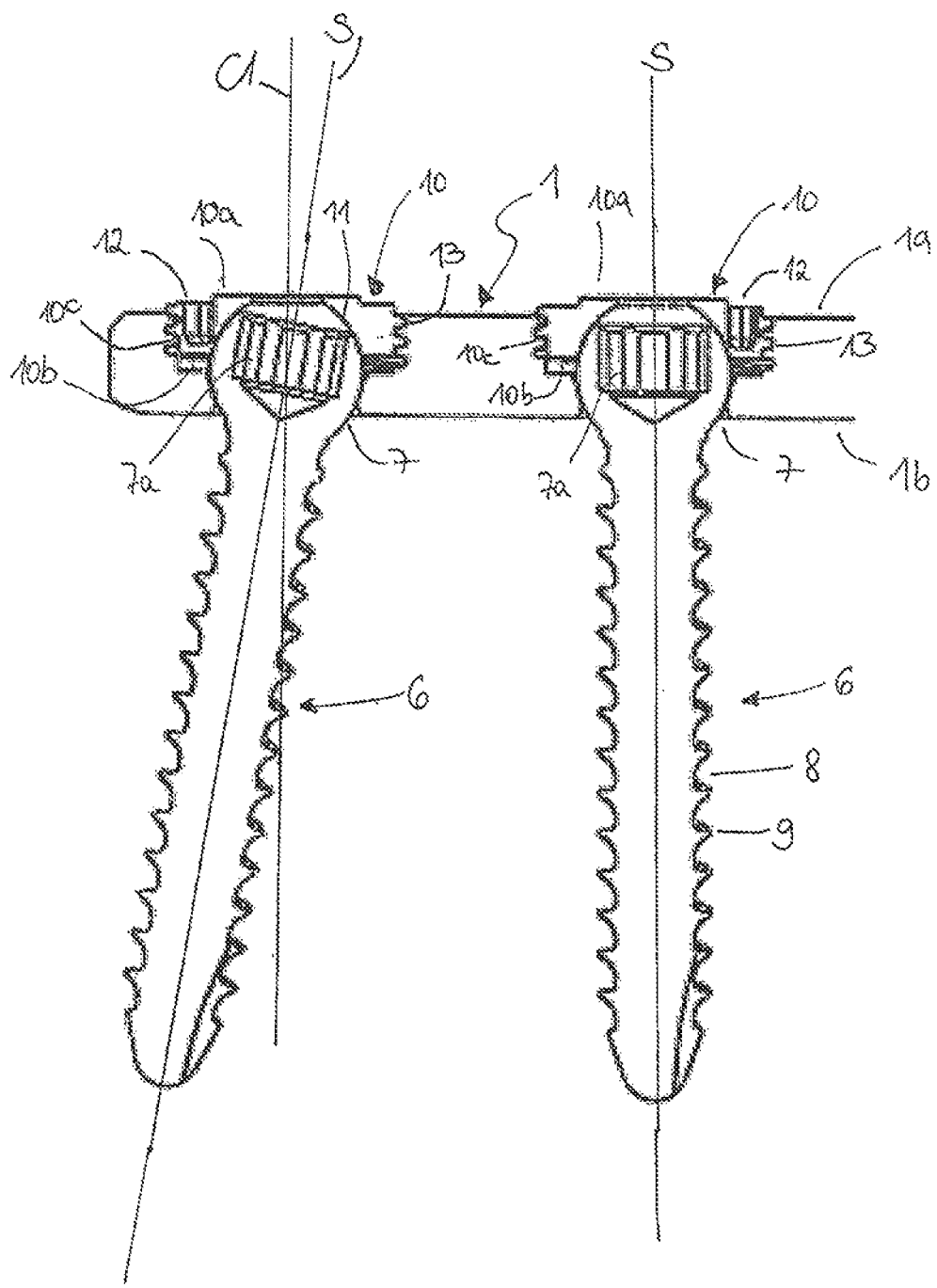
FIG. 3 shows a schematic cross-sectional sectional view of a bone fixation assembly with a hole, a screw and a locking element according to the first embodiment.

Moreover, the assembly may comprise a bone anchor 6 with a head 7 and a shank 8 as can be seen in FIG. 3. In this embodiment, the bone anchor 6 is a bone screw having a head 7 with a spherically-shaped outer surface portion and a shank 8 with a bone thread 9 and a shank axis S. Typically, the head has an engagement structure 7a for a driver.

The first bore 2a of the passage 2 has a first end open towards the top side 1a of the plate member 1. At the top side 1a, the first bore defines an edge 14. The first bore 2a has a circular cross-section bounded by the edge 14 and an internal thread 5 for engagement with a locking element 10. The thread 5 may extend along the full axial length or along a portion of the length of the bore 2a. Further, the first bore 2a has a diameter that is larger than the largest diameter of the head 7 of the bone anchor 6. As can be seen in FIGS. 1 and 3, the first bore 2a substantially extends into the plate member 1 and ends around half of the thickness of the plate member 1 at its second end, where it forms an annular shoulder 3 within the passage 2. This annular shoulder 3 defines a first plane P1 as can be seen in FIGS. 1 and 2. The first bore 2a further comprises a bore axis or central axis C1, being also the central axis of the first plane P1. In the case that the top side 1a is parallel to the bottom side 1b, C1 is perpendicular to the top side 1a and the bottom side 1b of the plate member 1. This facilitates insertion and tightening of the locking element and the risk of cross-threading is minimized.

The second bore 2b is of conical shape and is open towards the bottom side 1b of plate member 1 and forms an inner surface. At the bottom side 1b, the second bore defines a circular or elliptical edge 15. The diameter of the second bore 2b is at least equal to the smallest diameter of the seat portion 2c with an increasing inner diameter towards the open end at the bottom side 1b of the plate member.

The seat portion 2c is adapted to fully circumferentially support the head 7 of the bone anchor 6. The seat portion 2c is formed by a hollow spherical segment-shaped portion that extends between the first bore 2a and the second bore 2b with decreasing inner diameter towards the second bore 2b. A central axis C3 of symmetry of the seat, in the following seat central axis C3, extends through the seat portion 2c. The seat central axis C3 of the seat portion is inclined with respect to the central axis C1 of the first bore 2a by an angle α. In this embodiment, angle α is approximately 10°. The seat central axis C3 intersects the central axis C1 at a position in the passage 2 that corresponds to the center point of the sphere defined by the spherical seat 2c. By the tapering design of the seat portion 2c, an inwardly extending annular edge 4 is formed between the seat portion 2c and the second bore 2b. The inwardly extending annular edge 4 defines the smallest diameter of the passage 2. Moreover, by the inwardly extending annular edge 4 a second plane P2 is defined with the seat central axis C3 being perpendicular thereto. By means of this, the second plane P2 is tilted relative to the first plane P1 and intersects the plane P1 at the angle α. The Zero-position (0°-position) of the bone anchor 6 is defined by the shank axis S being coaxial to the seat central axis C3.

The seat portion 2c partially extends to the bottom side 1b of the plate member 1. As can be seen in FIG. 1, the lowermost portion of the seat portion 2c at one side with respect to the central axis C3 of the seat portion 2c may be at the bottom side 1b of the plate member 1, while the opposite side is at a distance from the bottom side 1b. However, the lowermost portion of the seat portion 2c may also be located at some distance from the bottom side 1b. The uppermost portion of the seat portion 2c can be at the first plane P1 or can merge into the first bore 2a.

Additionally, the passage 2 includes a third bore 2d being arranged between the first bore 2a and the seat portion 2c and connecting them. As can be seen in FIG. 1, the diameter of the third bore 2d is equal to or more than the largest diameter of the head 7 of screw 4 and may be smaller than the diameter of the first bore 2a. The head 7 may be guided by the third bore 2d when it is inserted.

The maximum angle of inclination that the shank axis S can assume with respect to the seat central axis C3 may be defined by the diameter of the bore 2a relative to the largest outer diameter of the head 7 and the size and position of the engagement structure 7a for the driver. Additionally, the width of the second bore 2b may limit the maximum angle of inclination. The pivot angle of the bone anchor in the seat portion or the insertion angle of the bone anchor around the seat central axis C3 is an angle β resulting in a total range of motion of 2β.

Since the seat central axis C3 defines the Zero-position of the bone anchor 6 as mentioned above, the bone anchor 6 shown in the left side of FIG. 3 is angled at the angle α relative to the central axis C1 of plane P1 in its Zero-position. Hence, the shank axis S of the bone anchor 6 is already angled with respect to the central axis C1 of the first bore 2a to the favored side in the Zero-position, which is 10° in this embodiment. Depending on the size of the first bore 2a and due to the design of the second bore 2b, it is possible to insert the bone anchor 6 into the bone at an angle of β relative to its Zero-position to the favored side. Consequently, the shank axis S of bone anchor 6 may be inclined to the favored side with a maximum angle that is the sum α+β which may be around 30° relative to the central axis C1 of the plane P1. As the motion cone is circular and thus symmetrical about the central axis C3, the angle of inclination to the side opposite from the favored side is reduced by the angle α starting from the bone anchor's Zero-position and thus is β−α in total. This however is not detrimental as the favored side is intended to be used for the angular position of the screw.

The position of the bone anchor 6 relative to the plate 1 can be locked or stabilized by the above-mentioned locking element 10. In the embodiment shown, the locking element 10 is substantially cylindrical with a top side 10a, a bottom side 10b opposite to the top side 10a and an outer surface portion 10c therebetween. The diameter of the locking element 10 corresponds to the diameter of the first bore 2a. In an assembled state, the bottom side 10b is facing the head 7 of the bone anchor 6. As can be seen in FIG. 3, a first recess 11 is provided at the bottom side 10b for accommodating at least a portion of the head 7. The recess 11 has a spherically-shaped inner surface portion corresponding to the spherically-shaped outer surface portion of the head 7. At the top side 10a, at least one further recess 12 is provided for engagement with a driver. Moreover, the locking element 10 comprises an external thread 13 on its outer surface portion 10c. The external thread 13 is configured to interact with the internal thread 5 of the plate member 1. The height of the locking element 10 is smaller than the depth of the threaded bore 2a into the plate member 1. It may be desirable that the top side 10a of the locking element 10 is substantially flush with the top side 1a of the plate member 1 when the head is locked by the locking element 10.

The plate member 1 may have a second passage 2' comprising a first bore 2a' with a central axis C1', a second bore 2b with a second bore axis C1' and a seat portion 2c' therebetween, having a central axis C3' and a third bore 2d' between the first bore 2a' and the seat portion 2c'. The first bore 2a' may be threaded. A shoulder 3' is formed between the first bore 2a' and the third bore 2d' within of the plate member 1, defining a plane P1' with a central axis C1' orthogonal thereto. Furthermore, the seat portion 2c' forms an inwardly extending annular edge 4' defining a second plane P2'. Contrary to passage 2 described before, the axes C1' and C3' extend coaxially through passage 2' and orthogonal to the top side 1a and the bottom side 1b of the plate member 1. Moreover, the planes P1' and P2' are extending in parallel to each other. Further, a bone anchor 6 and a locking element 10 may be provided, the locking element 10 for locking the bone anchor as explained above.

The plate member 1 may have several holes with passages of the type of the passage 2 and/or the passage 2'.

Now, use of the bone plate assembly according to the first embodiment will be described. Once the necessary numbers and types of the bone anchors are determined, the plate member 1 is positioned at the fracture site. Then, the bone anchors are inserted into the first type passage 2 and/or second type passage 2' and inserted into the bone parts at the desired angle. The spherical seat allows placement of the head of the screw in the hole at this angle. The bone anchor 6 inserted into the first passage type 2 can assume a 10° larger angle of inclination to the favored side compared to the bone anchor inserted into the second passage type 2'.

To further stabilize the connection between the bone anchor and the plate member the locking element 10 can optionally be used which is inserted into the first bore 2a, 2a' and tightened so that it locks the head 7. If desired, the different locking elements can be applied to different bone anchors in order to provide for full locking, frictional locking or no locking where the locking member only prevents pull-out of the screw as described above. It may be noted that locking elements without thread but with another locking structure may be used to lock the head 7.

Alternatively, the bone plate can be used without a locking element as a non-locking plate.

In a second embodiment of a so-called non-locking plate, the first bore 2a, 2a' may be provided threadless.

A third embodiment will be explained with reference to FIGS. 4 to 6. In this embodiment, the bone plate assembly comprises an elongate plate member 1" with a planar upper side 1a, a planar bottom side 1b being parallel to the planar upper side 1a, a first and a second side wall 1c and 1d and a first and a second curved side wall 1e and 1f. Further, the plate member 1" comprises a central longitudinal axis L and a vertical axis T being parallel to each of the central axes C1 and C1' respectively of the first bores 2a and 2a' respectively, wherein the vertical axis T extends orthogonally from the top side 1a and the bottom side 1b of the elongate plate member 1. Five holes I to V extend through the elongate plate member 1" on the longitudinal axis L, wherein the first four holes I to IV (from left to right) are formed by passages according to the first embodiment. Contrary, the fifth hole V comprises solely bores with one single common central axis.

As can best be seen in FIGS. 5 and 6, the orientation of the seat portions 2c is such that the Zero-positions of the first four screws 6a to 6d differ from the Zero-position of the fifth screw 6f. The Zero-position of the first four screws are tilted relative to Zero-position of the fifth screw by an angle, for example by approximately 10°, each in another direction of the four directions relative thereto. This may be useful in specific anatomical conditions. The number and the angle of the Zero-position may be adapted to such a specific condition.

A fourth embodiment will now be described with reference to FIG. 7. This embodiment comprises a bone plate assembly with an upwardly angled elongate plate member 1'". The bone plate member includes an upwardly angled bone plate portion 100 as well as a planar bone plate portion 101. Two passages extend through the angled bone plate portion 100 and four through the planar bone plate portion 101. Furthermore, the corresponding Zero-positions and the corresponding motion cones of a bone anchor are indicated. In this embodiment, the first and the second hole in the angled bone plate portion 100 have a design according to the first or the second embodiment allowing an increased insertion angle of a bone anchor in the direction of the inclination of the bone plate member 1'''.

Turning now to FIGS. 8 through 12, a fifth embodiment is shown. As will be described, the fifth embodiment of the bone plate is adapted to permit the bone anchor 6 to extend in a screw passage 202 in one favored direction at an angle up to 40° relative to the central axis C1 of the passage, and in an opposite direction up to 20° relative to the central axis C1 of the passage, providing a total of 60° angular displacement relative to the central axis C1 of the passage. The bone plate assembly of the fifth embodiment is of the locking type, but can also be used as a non-locking plate. The bone plate assembly includes a plate member 200 with a top side 201a, a bottom side 201b, the top side 201a and the bottom side 201b being substantially parallel to each other. A hole forming the passage 202 extends through the plate member 201 from the top side 201a to the bottom side 201b. The passage 202 is formed by three bores 202a, 202b, 202d, a seat portion 202c between the first and second bores 202a, 202b that is configured to receive and support the head 7 of the bone anchor 6, and first, second and third side recesses 230, 232, 234 adapted to permit increased displacement of a bone anchor in a favored angular direction.

Figure 8:
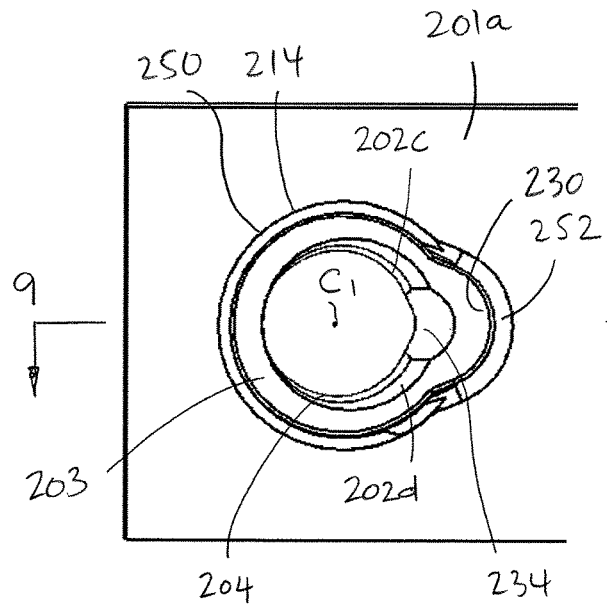
FIG. 8 shows a schematic top view of a plate member of a bone fixation assembly according to an embodiment.
Figure 10:
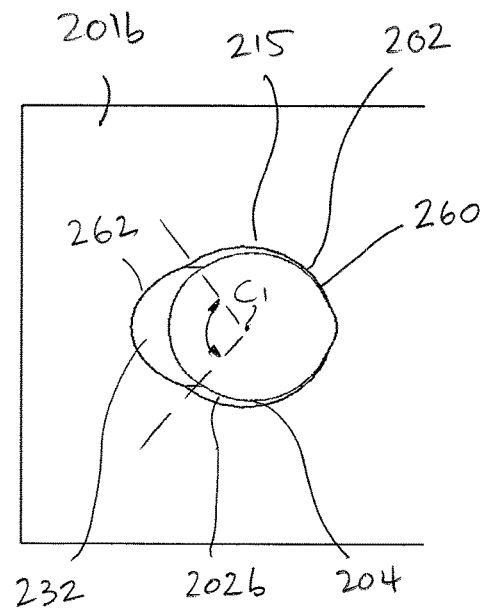
FIG. 10 shows a schematic bottom view of the plate member of FIG. 8.
Figure 9:
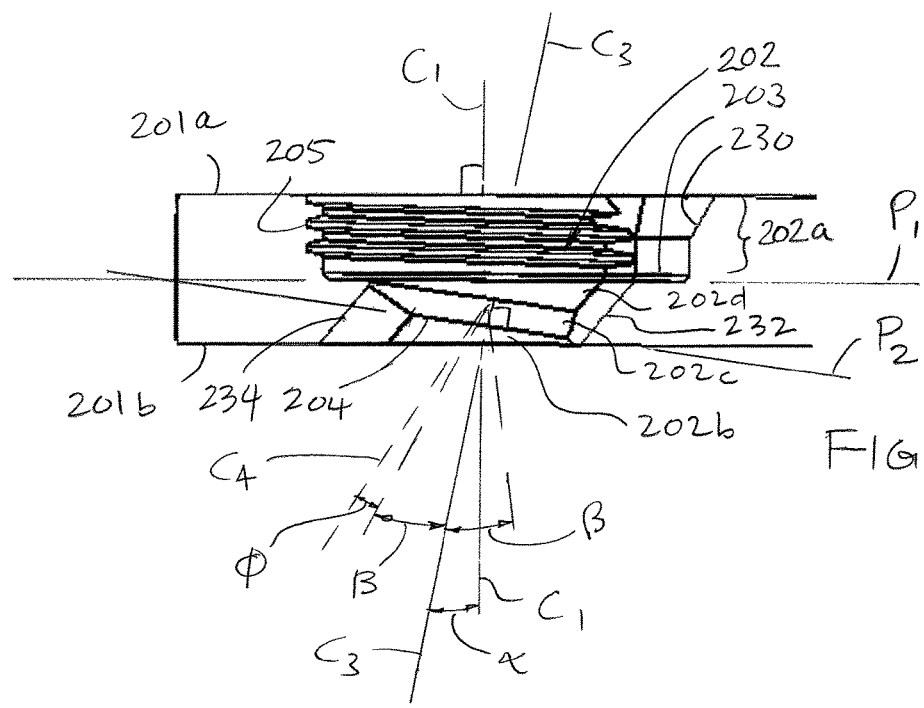
FIG. 9 shows a schematic cross-sectional view across line 9-9 in FIG. 8.

The first bore 202a of the passage 202 has a first end open towards the top side 201a of the plate member 201. At the top side 201a, the first bore 202a defines a first edge 214. The first edge 214 is preferably formed by a first portion 250 and a second portion 252. The first portion 250 extends concentrically about the bore axis or central axis C1 and has a first radius of curvature. The second portion 252 extends about the remainder of the perimeter, and away from the central axis C1 of the first bore 202a. In the embodiment shown, the second portion 252 of the first edge 214 has a second radius of curvature smaller than the first radius and is not concentric with the first bore 202a. In the case that the top side 201a is parallel to the bottom side 201b, central axis C1 is perpendicular to the top side 201a and the bottom side 201b of the plate member 201. The first portion 250 of the first bore 202a has an internal thread 205 for engagement with a locking element 10 (FIG. 12), whereas no internal thread is provided about the second portion 252 of the first bore 202a. The thread 205 may extend along the full axial length or along a portion of the length of the first bore 202a. The first bore 202a has a diameter that is larger than the largest diameter of the head 7 of the bone anchor 6 (FIG. 10). As can be seen in FIGS. 8 and 9, the first bore 202a substantially extends into the plate member 201 and ends around half of the thickness of the plate member 201 at its second end, where it forms an annular shoulder 203 within the passage 202. This annular shoulder 203 defines a first plane P1 perpendicular to C1. This facilitates insertion and tightening of the locking element 10 and minimizes the risk of cross-threading.

The second bore 202b is of conical shape, is open towards the bottom side 201b of plate member 201, and forms an inner surface that, at the bottom side 201b, defines a second edge 215. The second edge 215 includes a first portion 260 and a second portion 262. The first portion 260 of the second edge 215 extends about a portion of the perimeter of the second bore 202b and has a first radius of curvature that is concentric with central axis C1. The second portion 262 of the second edge 215 extends through an arc of 80° to 120° (measured relative to axis C1) at a side of second bore 202b opposite the extension of the second portion 252 of the first bore 202a. The diameter of the second bore 202b is at least equal to the smallest diameter of the seat portion 202c with an increasing inner diameter towards the open end at the bottom side 201b of the plate member.

The seat portion 202c is adapted to support the head 7 of the bone anchor 6. The seat portion 202c is formed by a hollow spherical segment-shaped portion that extends between the first bore 202a and the second bore 202b with decreasing inner diameter towards the second bore 202b. A central axis C3 of the seat extends through the seat portion 202c. The seat central axis C3 of the seat portion is inclined with respect to the central axis C1 of the first bore 202a by an angle $\alpha$. In this embodiment, angle $\alpha$ is approximately 10°; other angles are possible. The seat central axis C3 intersects the central axis C1 at a position in the passage 202 that corresponds to the center point of the sphere defined by the spherical seat 202c. By the tapering design of the seat portion 202c, an inwardly extending annular edge 204 is formed between the seat portion 202c and the second bore 202b. The inwardly extending annular edge 204 defines the smallest diameter of the passage 202. Moreover, by the inwardly extending annular edge 204, a second plane P2 is defined with the seat central axis C3 being perpendicular thereto. By means of this, the second plane P2 is tilted relative to the first plane P1 and intersects the plane P1 at the angle $\alpha$. The Zero-position (0°-position) of the bone anchor 6 is defined by the shank axis S being coaxial to the seat central axis C3.

The seat portion 202c may partially extend to the bottom side 201b of the plate member 201. As can be seen in FIGS. 9 and 10, the lowermost portion of the seat portion 202c at one side with respect to the central axis C3 of the seat portion 202c may be at the bottom side 201b of the plate member 201, while the opposite side is at a distance from the bottom side 201b. However, the lowermost portion of the seat portion 202c may also be located at some distance from the bottom side 201b. The uppermost portion of the seat portion 202c can be at the first plane P1 or can merge into the first bore 202a.

Figure 11:
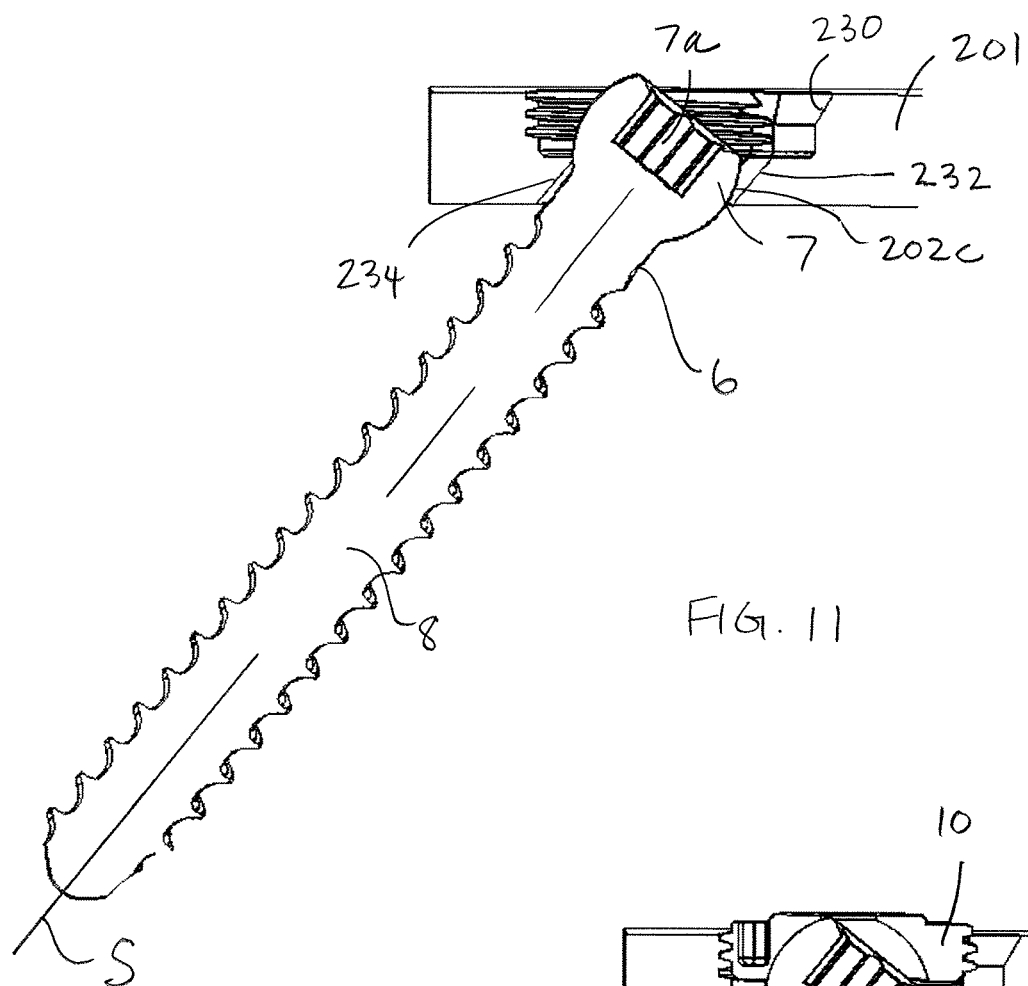
FIG. 11 shows a view similar to FIG. 8 with a bone screw inserted in a screw hole of the plate member.

Additionally, the passage 202 includes a third bore 202d being arranged between the first bore 202a and the seat portion 202c and connecting them. As can be seen in FIG. 11, the diameter of the third bore 202d is equal to or more than the largest diameter of the head 7 of bone anchor 6 and may be smaller than the diameter of the first bore 202a. The head 7 may be guided by the third bore 202d when it is inserted.

The first side recess 230 is defined at the intersection of the of the second portion 252 of the first edge 214 and the top side 201a of the plate 201. The top of the first side recess 230 angles outward, away from the central axis C1.

The second side recess 232 is bounded at the bottom side 201b by the second portion 262 of the second edge 215. The second side recess 232 extends through the second bore 202b, the seat 202d, the third bore 202c and the shoulder 203. The second side recess 232 is defined by a radius extending perpendicular to an axis C4 sufficiently large to receive the shaft 8 of the bone anchor 6 at a maximum favored angle relative to the central axis C1. In the embodiment shown, the maximum favored angle is 40° relative to central axis C1; the plate 201 and passage 202 can be adapted for other maximum favored angles.

The third side recess 234 extends through the seat portion 202c, the third bore 202d, and a portion of the shoulder 203, all on a same side of the passage 202 as the first side recess 230 and an opposite side from the second side recess 232.

From the above, the first and third side recesses 230, 234 provide clearance for the shaft 8 of the bone anchor 6 as the bone anchor is inserted through the passage 202 as well as for a driver to be engaged with the engagement structure 7a in the head 7 of the bone anchor when the bone anchor is oriented at an extreme angle, and the second side recess 232 provides clearance for the angled shaft 8.

In view of the above, it can be summarized that at least a majority of the first edge 215 has a first radius centered about the first central axis C1, and a minority of the first edge defines a first recess 230 extending away from the central axis C1 in a first direction, and at least a majority of the second edge 216 has a second radius centered about the second central axis C3, and a minority of the second edge 216 defines, at least in part, the second recess 234 extending away from the central axis C1 in a second direction opposite the first direction.

The maximum angle of inclination that the shank axis S can assume with respect to the seat central axis C3 may be defined by the width of the bore 202a relative to the largest outer diameter of the head 7 of the bone anchor 6 and the size and position of engagement structure 7a for the driver. The width is measured in a first direction. The maximum angle of inclination that the shank axis S can assume is also determined by the width of the second bore 202b measured in a second direction, parallel to and opposite the first direction. While the pivot angle of the bone anchor in the seat portion or the insertion angle of the bone anchor around the seat central axis C3 is an angle $\beta$, an angle $\phi$, accommodated by the first, second and third recesses 230, 232, 234 provides an additional range of motion toward a favored side aligned with the inclined angle $\beta$ relative to central axis C1, resulting in a total maximum angular motion of $2\beta+\phi$.

Since the seat central axis C3 defines the Zero-position of the bone anchor 6 as mentioned above, the bone anchor 6 shown in FIG. 11 is angled at an angle defined by the angle $\alpha$ relative to the central axis C1 of plane P1 in its Zero-position. Hence, the shank axis S of the bone anchor is already angled with respect to the central axis C1 of the first bore 202a to the favored side in the Zero-position, which is 10° in this embodiment. Depending on the size of the first bore 202a and due to the design of the second bore 202b, and in view of the first, second, and third side recesses, 230, 232, 234, it is possible to insert the bone anchor 6 into the bone plate at an angle of $\beta+\phi$ relative to its Zero-position to the favored side (or $\beta+\alpha+\phi$ relative to the central axis C1). Consequently, the shank axis S of bone anchor 6 may be inclined to the favored side with a maximum angle that is the sum $\beta+\alpha+\phi$, which may be around 40° relative to the central axis C1 of the plane P1. The motion cone in this embodiment is non-circular and asymmetrical about the central axis C3, extending further in the favored direction relative to the central axis C1. The angle of inclination to the side opposite from the favored side is reduced by the angle $\alpha$ starting from the bone anchor's Zero-position and thus is $\beta-\alpha$ in total. This however is not detrimental as the favored side is intended to be used for the angular position of the screw.

Figure 12:
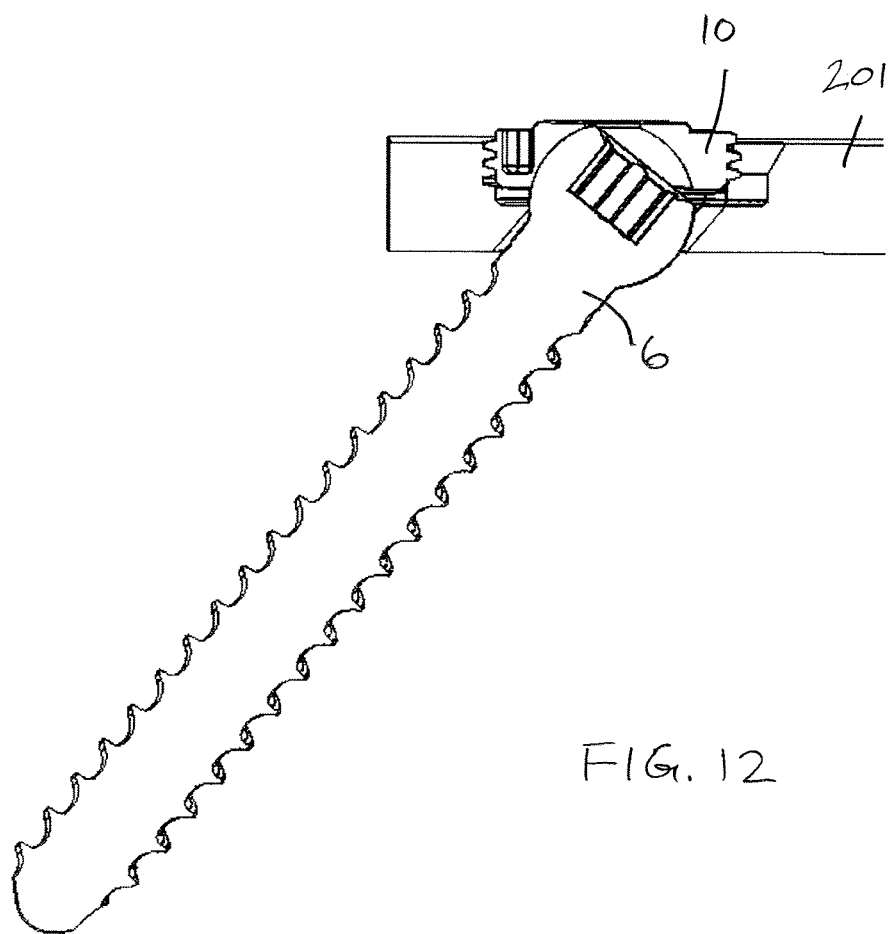
FIG. 12 shows a view similar to FIG. 8 with a bone screw and a locking element inserted in the screw hole of the plate member.

Turning to FIG. 12, the position of the bone screw 6 relative to the plate 201 can be locked or stabilized by the above-mentioned locking element 10.

Referring now to FIGS. 13 through 15, a sixth embodiment, substantially similar to the fifth embodiment (with like parts having reference numerals incremented by 100), is shown. The sixth embodiment is distinct from the fifth embodiment in the structure of the second side recess 332. The second side recess 332 is bounded at the bottom side 301b by the second portion 362 of the second edge 315. The second side recess 332 extends vertically through portions of the second bore 302b, the seat 302d, the third bore 302c and the shoulder 303. The second side recess 332 is defined by a radius r1 extending perpendicular to a vertical axis C5 displaced from and parallel to central axis C1. The radius r1 of C5 is preferably smaller than the radius of each of the first bore 302a, second bore, 302b, third bore 302c, and seat 302d. However, the radius r1 defines a recess 332 sufficiently large to receive the shaft 8 of the bone anchor 6 at the same maximum favored angle relative to the central axis C1 described with respect to the fifth embodiment. It is further appreciated that while the second side recess 332 is described as preferably defined by a radius r1 to provide the requisite clearance, the recess can be formed by another shape, including a curve with a non-constant radius or an angular channel.

Figure 16:
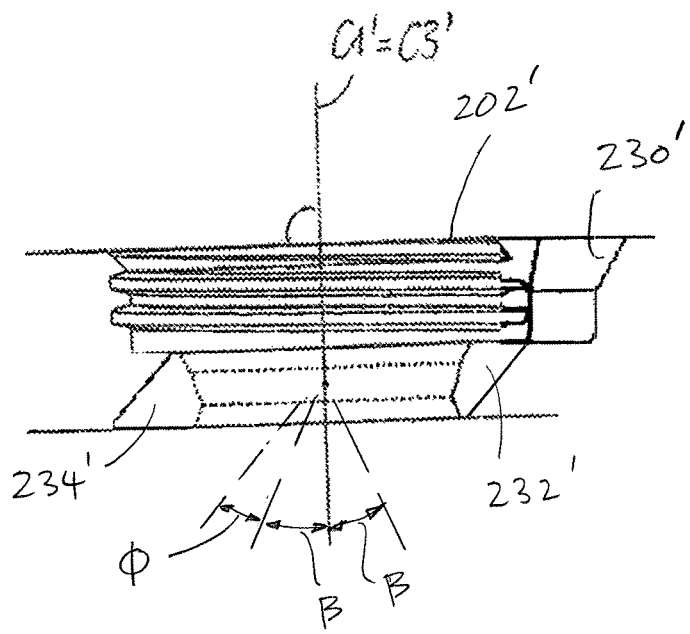
FIG. 16 shows a schematic cross-sectional view of another embodiment.

Turning now to FIG. 16, a seventh embodiment of a screw hole 202' is shown. The seventh embodiment has the same recesses 230', 232' and 234' as in the fifth embodiment, but has a central axis of the passage C1 and a central axis of the seat C3 extending coaxially. The recesses 230', 232', 234' allow a bone anchor to be angled a greater degree toward a favored direction than in other directions. With the Zero position of the bone anchor being coaxial with axes C1 and C3, the maximum angle in a favored direction is $\beta+\phi$ relative to its Zero-position (C1), whereas the maximum angle in other directions such as opposite the favored direction is $\beta$ only.

Figure 17:
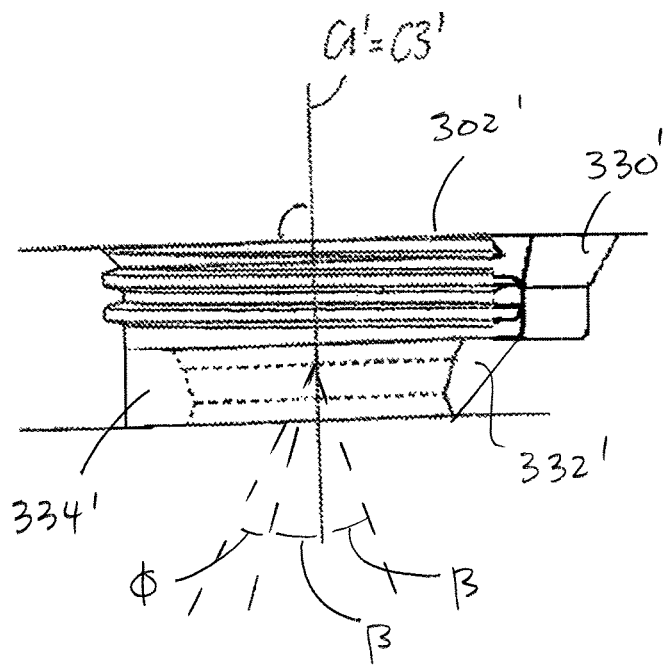
FIG. 17 shows a schematic cross-sectional view of yet another embodiment.

Referring now to FIG. 17, an eighth embodiment of a screw hole 302' is shown. The eighth embodiment has the same recesses 330', 332' and 334' as in the sixth embodiment, but has a central axis of the passage C1 and a central axis of the seat C3 extending coaxially. The recesses 330', 332', 334' allow a bone anchor to be angled a greater degree toward a favored direction than in other directions. With the Zero position of the bone anchor being coaxial with axes C1 and C3, the maximum angle in a favored direction is $\beta+\phi$ relative to its Zero-position (C1), whereas the maximum angle in other directions such as opposite the favored direction is $\beta$ only.

Further embodiments are possible. For example, the first bore 2a may be conically-shaped tapering towards the lower side with a smallest diameter being equal to the largest diameter of a screw head. In a still further embodiment, the second bore 2b may be cylindrically-shaped with such a size that it limits the angle $\beta$. In a specific embodiment $\beta$ may be zero so that the shank axis S can assume only the angle $\alpha$ with respect to the central axis C1 of the first bore 2a.

Furthermore, the seat may be conically-shaped or otherwise shaped, such that the seat and the head of the bone anchor form a ball- and socket-joint.

Plane P1 may be tilted with respect to the top side 1a and/or the bottom side 1b. This may be the case if the top side 1a and the bottom side 1b are not substantially parallel or have an irregular structure.

Moreover, the bone plate may have additionally or instead an alternative hole configured to receive an insert, wherein the insert comprises the angled seat portion 2c as described above.

It should be clear from the above that the number, the design (for example in terms of the orientation and the extent of the enlarged angle of inclination) as well as the arrangement of the different holes can be varied according to the anatomical situation. For example, the holes may be offset from the central longitudinal axis L. The shape of the bone plate may be elongate, rectangular or otherwise shaped and/or curved and may have different sizes. Moreover, different embodiments can be combined among each other to provide a specific plate member needed for a specific application.

Instead of the bone screw with a threaded shank any other bone anchor having a shank for anchoring in the bone, such as for example a bone nail, with or without barbs, can be used. The shank may also be cannulated and may have openings in the wall to allow introduction of bone cement or other substances.

The elements of the bone plate assembly are made of a body compatible material, such as a body compatible metal, for example stainless steel or titanium or a body compatible metal alloy such as Ni—Ti alloys, for example Nitinol, or of a body compatible plastic material, for example medical grade PEEK or of a combination thereof. For example, the plate member and the bone anchors can be made of different materials.

While the bone plate members have been shown in the exemplar embodiments as bone plates for use with bone anchors, it is recognized that the plate members may be adapted for other fixation assemblies. By way of example, the plate member may be a component of a prosthetic joint. By way of further example, the plate member may be a baseplate component of a shoulder prosthesis. By way of more specific example, the plate member may be a glenoid baseplate for reverse arthroplasty of the shoulder. That said, the plate member is not limited to fracture fixation plates and prosthetic baseplates. The plate member may be a plate-like member of an orthopedic implant or implant system for surgical implantation into the body.

Moreover, the primary use of the plate member is anticipated to be human implantation for orthopaedic or trauma surgery. However, the plate member may be readily adapted in size for veterinary use and may be used in any animal, in particular mammals.

What is claimed is:

1. A plate member for use with a bone anchor having a head and a shank, the plate member comprising:
    a plate member having a top side and a bottom side, the plate member defining at least one passage extending from the top side to the bottom side, wherein the at least one passage includes,
    a first bore with a first end and a second end, the first bore defining a first central axis between the first and second ends, the first end intersecting the top side at a first edge,
    a seat portion configured to receive, contact, and support the head of the bone anchor, the seat portion comprising a second central axis,
    a second bore having a first end and a second end, the second end intersecting the bottom side at a second edge,
    wherein a majority of the first edge has a first radius centered about the first central axis, and a minority of the first edge defines a first clearance extending outside the first radius which is adapted in size for receiving at least one of the shank and the head to pass through at an angle relative to first and second central axes, and
    wherein a majority of the second edge has a second radius, and a minority of the second edge defines a second clearance extending outside the second radius which is adapted in size for receiving the shank at a shank angle extending along a shank axis angled relative to the first and second central axes,
    wherein the first clearance and the second clearance extend in opposite directions from each other and are located on diametrically opposite sides of the first central axis.

2. The plate member according to claim 1, wherein the second clearance is a concave recess in the bottom side.

3. The plate member according according to claim 2, wherein the second clearance is defined by a third radius smaller than the first and second radii.

4. The plate member according according to claim 1, wherein the second clearance is formed by a portion of a hole with a third radius smaller than the first radius.

5. The plate member according according to claim 4, wherein the hole is angled relative to the first axis, and the third radius extends from the shank axis.

6. The plate member according to claim 1, wherein the shank angle is greater than 30° relative to the first central axis.

7. The plate member according according to claim 1, wherein the shank angle is up to 40° relative to the first central axis.

8. The plate member according according to claim 1, wherein the second central axis is angled relative to the first central axis.

9. The plate member according to claim 8, wherein the first central axis and the second central axis intersect each other within the seat portion.

10. The plate member according according to claim 1, wherein the first and second central axes are coaxial.

11. A plate member for use with a bone anchor having a head and a shank, the plate member comprising:
    a plate member having a top side and a bottom side, the plate member defining at least one passage extending from the top side to the bottom side, wherein the at least one passage includes,
    a first bore with a first end and a second end, the first bore defining a first central axis between the first and second ends, the first end intersecting the top side at a first edge, at least a portion of the first edge defining a first recess extending away from the first central axis in a first direction,
    a hollow spherical segment-shaped seat portion configured to receive, contact, and support the head of the bone anchor, the seat portion comprising a second central axis,
    a second bore having a first end and a second end, the second end intersecting the bottom side at a second edge, at least a portion of the second edge defining a second recess in the bottom side extending away from the first central axis in a second direction opposite the first direction, the first and second recesses located on diametrically opposite sides of the first central axis.

12. The plate member according to claim 11, wherein a surface defining the seat portion has a circular shape in a cross-sectional plane transverse to the second central axis.

13. The plate member according to claim 11, wherein the passage of the plate member includes a third bore provided between the first bore and the seat portion and open towards the first bore and the seat portion, wherein the third bore has a diameter that is at least equal to a largest diameter of the seat portion and smaller than a smallest diameter of the first bore, and wherein the third bore tapers in diameter along the second central axis from the first bore to the seat portion.

14. The plate member according to claim 11, wherein the second end of the first bore defines a first plane and wherein an inwardly extending lower edge of the seat portion that faces towards the bottom side defines a second plane, and wherein the first plane and the second plane intersect each other at a non-zero angle α.

15. The plate member according to claim 14, wherein the angle α is approximately 1 to 20°.

16. The plate member according to claim 11, wherein the second bore has a diameter that is at least equal to a smallest diameter of the seat portion.

17. The plate member according to claim 11, wherein an inner diameter of the second bore increases towards the open end at the bottom side of the plate member.

18. The plate member according to claim 11, wherein the first bore comprises an internal thread.

19. The plate member according to claim 11, wherein the first bore is substantially cylindrical.

20. The plate member according to claim 11, wherein a majority of the first edge has a first radius centered about the first central axis.

21. The plate member according to claim 20, wherein a minority of the first edge defines the first recess.

22. The plate member according to claim 20, wherein a majority of the second edge has a second radius centered about the second central axis.

23. The plate member according to claim 22, wherein a minority of the second edge defines the second recess.

24. The plate member according to claim 11, wherein the second central axis is angled relative to the first central axis.

25. The plate member according to claim 24, wherein the first central axis and the second central axis intersect each other within the passage.

26. The plate member according to claim 11, wherein the first central axis and the second central axis are coaxial.

27. A plate member assembly for implantation into a mammalian body, comprising:
   a plate member having a top side and a bottom side, the plate member defining at least one passage extending from the top side to the bottom side, wherein the at least one passage includes,
      a first bore with a first end and a second end, the first bore defining a first central axis between the first and second ends, the first end intersecting the top side at a first edge,
      a seat portion configured to receive, contact, and support a spherical portion of the head of the bone anchor, the seat portion comprising a second central axis,
      a second bore having a first end and a second end, the second end intersecting the bottom side at a second edge,
      wherein a majority of the first edge has a first radius centered about the first central axis, and a minority of the first edge defines a first clearance outside the first radius for receiving at least one of the shank and the head at an angle relative to first and second central axes, and
      wherein a majority of the second edge has a second radius, and a minority of the second edge defines a second clearance outside the second radius for receiving the shank at a shank angle extending along a shank axis angled relative to the first and second central axes,
      wherein the first clearance and the second clearance extend in opposite directions from each other and are located on diametrically opposite sides of the first central axis; and
   a bone anchor including a head having a spherical portion receivable in the seat portion, and a shank defining a shank axis, wherein,
      the head is receivable in the seat portion such that the shank axis is at a zero-position coaxial with the second central axis, and
      the head is also receivable in the seat portion such that the shank is oriented into the shank angle such that the shank axis is angled relative to the first and second axes and the shank rests within the second clearance.

28. The plate member assembly according to claim 27, wherein the bone anchor and passage are configured such that the bone anchor can pivot in the seat portion more than 30° relative to the first central axis in a favored direction.

29. The plate member assembly according to claim 27, wherein the bone anchor and passage are configured such that the bone anchor can pivot in the seat portion up to 40° relative to the first central axis in a favored direction.

30. The plate member assembly according to claim 27, wherein the second central axis is angled relative to the first central axis.

31. The plate member assembly according to claim 30, wherein the first central axis and the second central axis intersect each other within the passage.

32. The plate member assembly according to claim 27, wherein the first central axis and the second central axis are coaxial.

33. The plate member assembly according to claim 27, further comprising a locking element configured to be received in the first bore and maintain a position of the bone anchor in the seat portion.

34. The plate member assembly according to claim 33, wherein the locking element is substantially cylindrical with a bottom side configured to face a head of a bone anchor, a top side opposite to the bottom side of the locking element, and wherein the locking element has a first recess at the bottom side of the locking element for accommodating at least a portion of the head and a second recess at the top side of the locking element for engagement with a driver.

35. A plate member assembly, comprising: a plate member,
   the plate member having a top side and a bottom side and defining at least one passage extending from the top side to the bottom side, wherein the at least one passage includes,
   a first bore with a first end and a second end, the first bore defining a first central axis between the first and second ends, the first end intersecting the top side at a first edge, at least a portion of the first edge defining a first recess extending away from the central axis in a first direction,
   a seat portion comprising a second central axis,
   a second bore having a first end and a second end, the second end intersecting the bottom side at a second edge, at least a portion of the second edge defining a second recess in the bottom side extending away from the first central axis in a second direction opposite the first direction, the first and second recesses located on a diametrically opposite sides of the first central axis; and
   a bone anchor including a head receivable in the seat portion, and a shank defining a shank axis, wherein,
      the head is receivable in the seat portion such that the shank axis is at a zero-position coaxial with the second central axis, and the head is also receivable in the seat portion such that the shank is oriented at a shank angle relative to the zero-position such that the shank axis is angled relative to the first and second axes and the shank rests within the second recess.

36. The plate member assembly according to claim 35, wherein the bone anchor and passage are configured such that the bone anchor can pivot in the seat portion more than 30° relative to the first central axis in a favored direction.

37. The plate member assembly according to claim 35, wherein the bone anchor and passage are configured such that the bone anchor can pivot in the seat portion up to 40° relative to the first central axis in a favored direction.

38. The plate member assembly according to claim 35, wherein the second central axis is angled relative to the first central axis.

39. The plate member assembly according to claim 38, wherein the first central axis and the second central axis intersect each other within the passage.

40. The plate member assembly according to claim 35, wherein the first central axis and the second central axis are coaxial.

41. The plate member assembly according to claim 35, further comprising a locking element configured to be received in the first bore and maintain a position of the bone anchor in the seat portion.

42. The plate member assembly according to claim 41, wherein the locking element is substantially cylindrical with a bottom side configured to face a head of a bone anchor, a top side opposite to the bottom side of the locking element, and wherein the locking element has a first recess at the bottom side of the locking element for accommodating at least a portion of the head and a second recess at the top side of the locking element for engagement with a driver.

43. The plate member assembly according to claim 35, wherein the head of the anchor has a spherical portion for contact with the seat portion.

* * * * *